United States Patent [19]

Han et al.

[11] Patent Number: 5,053,576

[45] Date of Patent: Oct. 1, 1991

[54] PROCESS FOR UPGRADING METHANE TO HIGHER HYDROCARBONS

[75] Inventors: Scott Han, Lawrenceville, N.J.; Robert E. Palermo, New Hope, Pa.; Judy A. Pearson, Point Pleasant, N.J.; Dennis E. Walsh, Richboro, Pa.

[73] Assignee: Mobil Oil Corporation, Fairfax, Va.

[21] Appl. No.: 456,703

[22] Filed: Dec. 26, 1989

[51] Int. Cl.$^5$ ................................................. C07C 2/00
[52] U.S. Cl. ..................................... 585/500; 585/943; 585/700; 585/750; 585/533
[58] Field of Search ............... 585/500, 443, 750, 700, 585/533

[56] References Cited

U.S. PATENT DOCUMENTS

| | | |
|---|---|---|
| 2,061,598 | 11/1936 | Smith et al. ........................ 585/500 |
| 4,670,619 | 6/1987 | Withers, Jr. et al. ................ 585/500 |
| 4,831,204 | 5/1989 | Kushnerick et al. ................ 585/533 |
| 4,831,205 | 5/1989 | Krambeck et al. .................. 585/533 |
| 4,849,571 | 7/1989 | Gaffney ............................... 585/500 |
| 4,851,602 | 7/1989 | Harandi et al. ..................... 585/533 |
| 4,879,424 | 11/1989 | Harandi et al. .................... 585/533 |

Primary Examiner—Patrick P. Garvin
Assistant Examiner—E. D. Irzinski
Attorney, Agent, or Firm—Alexander J. McKillop; Charles J. Speciale; Edward F. Kenehan, Jr.

[57] ABSTRACT

There is provided a process for the direct partial oxidation of methane with oxygen, whereby organic compounds comprising higher hydrocarbons are produced. The catalyst used in this reaction is a ZnZSM-5 catalyst. This catalyst may be prepared by ion exchanging or impregnating a ZSM-5 catalyst with a suitable zinc salt such as zinc nitrate.

3 Claims, No Drawings

PROCESS FOR UPGRADING METHANE TO HIGHER HYDROCARBONS

BACKGROUND

There is provided a process for the direct partial oxidation of methane with oxygen, whereby organic compounds comprising liquid hydrocarbons are produced. The catalyst used in this reaction is a ZnZSM-5 catalyst.

Natural gas is an abundant fossil fuel resource. Recent estimates places worldwide natural gas reserves at about $35 \times 10^{14}$ standard cubic feet, corresponding to the energy equivalent of about 637 billion barrels of oil.

The composition of natural gas at the wellhead varies but the major hydrocarbon present is methane. For example the methane content of natural gas may vary within the range of from about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Processed natural gas, consisting essentially of methane, (typically 85-95 volume percent) may be directly used as clean burning gaseous fuel for industrial heat and power plants, for production of electricity, and to fire kilns in the cement and steel industries. It is also useful as a chemicals feedstock, but large-scale use for this purpose is largely limited to conversion to synthesis gas which in turn is used for the manufacture of methanol and ammonia. It is notable that for the foregoing uses no significant refining is required except for those instances in which the wellhead-produced gas is sour, i.e., it contains excessive amounts of hydrogen sulfide. Natural gas, however, has essentially no value as a portable fuel at the present time. In liquid form, it has a density of 0.415 and a boiling point of minus 162° C. Thus, it is not readily adaptable to transport as a liquid except for marine transport in very large tanks with a low surface to volume ratio, in which unique instance the cargo itself acts as refrigerant, and the volatilized methane serves as fuel to power the transport vessel. Large-scale use of natural gas often requires a sophisticated and extensive pipeline system.

A significant portion of the known natural gas reserves is associated with fields found in remote, difficulty accessible regions. For many of these remote fields, pipelining to bring the gas to potential users is not economically feasible.

Indirectly converting methane to methanol by steam-reforming to produce synthesis gas as a first step, followed by catalytic synthesis of methanol is a well-known process. Aside from the technical complexity and the high cost of this two-step, indirect synthesis, the methanol product has a very limited market and does not appear to offer a practical way to utilize natural gas from remote fields. The Mobil Oil Process, developed in the last decade provides an effective means for catalytically converting methanol to gasoline, e.g. as described in U.S. Pat. No. 3,894,107 to Butter et al. Although the market for gasoline is huge compared with the market for methanol, and although this process is currently used in New Zealand, it is complex and its viability appears to be limited to situations in which the cost for supplying an alternate source of gasoline is exceptionally high. There evidently remains a need for other ways to convert natural gas to higher valued and/or more readily transportable products.

A reaction which has been extensively studied for many years is the direct partial oxidation of methane to methanol. This route, involving essentially the reaction of methane and gaseous oxygen according to the simple equation

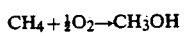

$$CH_4 + \tfrac{1}{2}O_2 \rightarrow CH_3OH$$

could theoretically produce methanol with no by-product. The homogeneous reaction of methane with oxygen to produce methanol occurs most favorably under high pressure (10 to 200 atm.), moderate temperatures, (350°-500° C.), and at relatively low oxygen concentration. Oxidation to formaldehyde and deep oxidation reactions are minimized under these conditions. The mechanism of methanol formation is believed to involve the methylperoxy radical ($CH_3OO \cdot$) which abstracts hydrogen from methane. Unfortunately, the per pass yields have been limited. This limited yield has been rationalized as resulting from the low reactivity of the C—H bonds in methane vis-a-vis the higher reactivity of the primary oxygenated product, methanol, which results in selective formation of the deep oxidation products CO and $CO_2$ when attempts are made to increase conversion.

U.S. Pat. No. 4,618,732 to Gesser et al. describes an improved homogeneous process for converting natural gas to methanol. The alleged high selectivity for methanol is ascribed by the inventors to careful premixing of methane and oxygen and to eliminating reactor wall effects by use of glass-lined reactors.

SUMMARY

There is provided a process for synthesizing a mixture of organic compounds comprising higher hydrocarbons including $C_5+$ liquid hydrocarbons by the direct partial oxidation of methane, said process comprising the steps of:
(i) contacting a mixture methane and oxygen with a ZnZSM-5 catalyst under sufficient conversion conditions; and
(ii) recovering said mixture of organic compounds comprising higher hydrocarbons.

It will be understood that the expression, higher hydrocarbons, as used herein, means hydrocarbons which have more carbon atoms (i.e. at least 2 carbon atoms) than methane. It will be further understood that the expression, $C_5+$ liquid hydrocarbons, as used herein, means liquid hydrocarbons which have at least 5 carbon atoms.

EMBODIMENTS

The ZnZSM-5 catalyst comprises an intimate mixture of Zn and ZSM-5 in a catalytically active form. This catalyst may be prepared by ion exchanging or impregnating ZSM-5 with a suitable zinc salt. This ion exchange or impregnation may take place using either a bound or unbound (i.e., binder free) form of ZSM-5. An example of a bound form of ZSM-5 is an extrudate of ZSM-5 and an alumina binder.

The zinc salt which is ion exchanged or impregnated with ZSM-5 may be a salt which is capable of being converted to zinc oxide upon calcination, especially in the presence of oxygen. An example of such a zinc salt is zinc nitrate.

In the practice of the present invention, it is preferred to use a dual flow system, i.e., a system in which the natural gas and the oxygen or air are kept separate until mixed just prior to being introduced into the reactor. However, if desired, the oxygen and natural gas may be premixed and stored together prior to the reaction. The preferred dual flow system minimizes the risk of fire or explosion. In the dual flow system, the amount of oxygen flow may be controlled so as to prepare a reaction mixture that contains 2 to 20 percent by volume, more preferably 3 to 15 percent of oxygen. Air may be used instead of oxygen without affecting the reaction. The gas hourly space velocity (GHSV) on zeolite may be within the range of about 100 to 100,000 $hr^{-1}$, preferably about 1,000 to 10,000 $hr^{-1}$, and most preferably about 2,000 to 8,000 $hr^{-1}$.

The temperature in the reaction zone may be from about 300° C. to 500° C., and preferably about 350° C. to 475° C. In the preferred mode of operation, the reactor temperature is increased until substantially all of the oxygen is consumed by the reaction, i.e., greater than about 90 percent $O_2$ consumption, and then it is held at about that temperature until further adjustment is required.

COMPARATIVE EXAMPLE A

An (H)ZSM-5 catalyst having a silica to alumina ratio of 70:1 was mixed with alumina (65% zeolite, 35% binder) and formed into extrudate. The extrudate, ground to 20–40 mesh, (8.0 cc) was mixed with an equal volume of sand and loaded into the reactor's 9/16 inch I.D. pyrex glass liner.

Feed mixtures were prepared from ultra high purity methane and C.P. grade oxygen supplied by Matheson, and the feed was passed over (H)ZSM-5 catalyst. Reaction conditions and the results of the experiments are included in Table I.

COMPARATIVE EXAMPLE B

PtZSM-5 was prepared by ion-exchanging 10 g of the Comparative Example A catalyst with 2.7 g of $Pt(NH_3)_4(NO_3)_2$ in 200 g $H_2O$ for 24 h at 25° C. The resultant catalyst was washed with water, dried and air-calcined.

This PtZSM-5 catalyst was contacted with a mixture of methane and oxygen in the manner described in Comparative Example A. Reaction conditions and results are included in Table I.

COMPARATIVE EXAMPLE C

CrZSM-5 was prepared by ion-exchanging 15 g of the Comparative Example A catalyst with 4.2 g $Cr(NO_3)_3.9H_2O$ in 200 g $H_2O$ for 24 h at 25° C. The resultant catalyst was washed with water, dried and air-calcined.

This CrZSM-5 catalyst was contacted with a mixture of methane and oxygen in the manner described in Comparative Example A. Reaction conditions and results are included in Table I.

EXAMPLE 1

ZnZSM-5 was prepared by ion-exchanging 15 g of the Comparative Example A catalyst with 3.1 g $Zn(NO_3)_2.6H_2O$ in 200 g $H_2O$ for 24 h at 25° C. The resultant catalyst was washed with water, dried and air-calcined.

This ZnZSM-5 catalyst was contacted with a mixture of methane and oxygen in the manner described in Comparative Example A. Reaction conditions and results are included in Table I.

EXAMPLE 2

The catalyst loading used in this Example was the same used in Example 1. This catalyst loading was contacted with a mixture of methane and oxygen and collection began after 8 hours time on stream. Reaction conditions and results are included in Table I.

TABLE 1

| | Catalytic Data and Results | | | | |
| | Example or Comparative Example | | | | |
| | A | B | C | 1 | 2 |
|---|---|---|---|---|---|
| Catalyst | HZSM-5 | PtZSM-5 | CrZSM-5 | ZnZSM-5 | ZnZSM-5 |
| Time on Stream | fresh | fresh | fresh | fresh | >8 hrs |
| Pressure, psig | 960 | 960 | 960 | 960 | 960 |
| Temp., °C. | 450 | 450 | 440 | 440 | 440 |
| GHSV (zeolite), $hr^{-1}$ | 4600 | 4600 | 4600 | 4600 | 4600 |
| Feed | | | | | |
| $CH_4$, % | 93.1 | 93.0 | 93.2 | 93.6 | 93.3 |
| $O_2$, % | 6.9 | 7.0 | 6.8 | 6.4 | 6.7 |
| $CH_4$ conv., % | 5.2 | 4.7 | 5.2 | 3.9 | 4.3 |
| Selectivities, % | | | | | |
| $CO_x$ | 83.3 | 97.2 | 99.2 | 93.3 | 81.6 |
| Oxygenates | 16.7 | 1.8 | 0.8 | 0.8 | 0.5 |
| $C_2-C_4$ | 0.0 | 1.0 | 0.0 | 0.4 | 5.6 |
| $C_5+$ | 0.0 | 0.0 | 0.0 | 5.5 | 12.3 |

As the data in Table 1 clearly show, addition of Zn to the ZSM-5 catalyst greatly improved the $C_2-C_4$ and $C_5+$ selectivities from methane at similar conversions. $C_5+$ liquids are not produced from methane/oxygen feeds over unmodified ZSM-5, CrZSM-5 or PtZSM-5 under similar conditions.

What is claimed is:

1. A process for synthesizing a mixture of organic compounds comprising higher hydrocarbons including $C_5+$ liquid hydrocarbons by the direct partial oxidation of methane, said process comprising the steps of:

(i) contacting a mixture of methane and oxygen with a ZnZSM-5 catalyst under sufficient conversion conditions including a temperature of from about 350° C. to about 475° C. and a pressure of from about 150 psig to about 3000 psig; and (ii) recovering said mixture of organic compounds comprising higher hydrocarbons.

2. A process according to claim 1, wherein said mixture of methane and oxygen contains from about 3 to about 20 percent by volume of $O_2$.

3. A process according to claim 1, wherein the catalyst is an aged ZnZSM-5 catalyst.

* * * * *